United States Patent [19]

Cerami

[11] 4,362,711

[45] Dec. 7, 1982

[54] BLOOD CHOLESTEROL LEVEL REDUCING AGENT AND METHOD

[75] Inventor: Anthony Cerami, Flanders, N.J.

[73] Assignee: Evreka Inc., Flanders, N.J.

[21] Appl. No.: 167,706

[22] Filed: Jul. 11, 1980

[51] Int. Cl.$^3$ ............... A01N 25/28; A61K 9/50; B01J 13/02

[52] U.S. Cl. .................... 424/33; 252/316; 424/32; 424/35; 424/37; 424/DIG. 6

[58] Field of Search ............ 252/316; 424/25, 33, 424/DIG. 6; 210/645, 927

[56] References Cited

U.S. PATENT DOCUMENTS

| | | | |
|---|---|---|---|
| 3,041,289 | 6/1962 | Katchen et al. | 252/316 |
| 3,725,113 | 4/1973 | Chang | 424/35 X |
| 4,046,750 | 9/1977 | Rembaum | 424/25 X |
| 4,201,822 | 5/1980 | Cowsar | 252/316 X |

FOREIGN PATENT DOCUMENTS 873815  6/1971  Canada ............... 252/316

*Primary Examiner*—Richard D. Lovering
*Attorney, Agent, or Firm*—David A. Jackson; Daniel H. Bobis

[57] ABSTRACT

An agent for reducing the cholesterol level in the blood of a warm blooded animal comprises a plurality of vesicles prepared from a non-toxic, non-biodegradable, semi-permeable material, and a quantity of a bile acid sequestrant provided in liquid form. The liquid sequestrant is disposed within the vesicles in an amount by volume of up to ninety percent of the available internal volume of the vesicle. The vesicles selectively permit the ingress of bile acids, and may preferably possess an electrical charge on their outer surface to assist the passage of the bile acids therethrough.

The present invention includes a method for reducing the cholesterol level in the blood, comprising administering the reducing agent. Oral administration is preferred, and, in one embodiment, the reducing agent comprising a plurality of the vesicles may be contained within a capsule or the like.

18 Claims, No Drawings

BLOOD CHOLESTEROL LEVEL REDUCING AGENT AND METHOD

BACKGROUND OF THE INVENTION

The present invention relates to the reduction of cholesterol levels in the blood supply of warm blooded animals, and particularly in humans.

The condition known as atherosclerosis has long been recognized as a major contributor to death due to cardiovascular failure. Particularly, it is determined that certain deposits of fatty tissue, known as lipids develop on the internal walls of arteries, and cause constrictions which drastically reduce blood flow and place greater strain on the heart. Also, these fatty deposits frequently dislodge and form emboli that can lodge in other vessels and result in their total blockage. Though a variety of causes have been outlined and are under study, the development of the condition, known as hyperlipidemia, wherein such fatty deposits form, has been studied and determined to be directly related to excessively high levels of the compound cholesterol in the blood stream. Specifically, increased risk for premature ischemic heart disease in young men has been found when the cholesterol concentration exceeds two hundred and twenty (220) milligrams per one hundred (100) milliliters of blood plasma.

A variety of treatments have been developed in recent years and proposed for reducing the cholesterol level in the blood. Specifically, one of the approaches has been to sequester or complex bile acids and remove them from the system. It has been found that when the bile acids are so removed from the enterohepatic circulation, there is an increased hepatic conversion of cholesterol to bile acids. Thus, in instances where bile acid levels were reduced, cholesterol levels dropped. Specifically, cholestyramine, a resinous bile acid sequestrant comprising a copolymer of styrene and divinyl benzene and containing trimethyl benzyl ammonium groups, was administered in amounts of 12 to 28 grams to human test patients, and cholesterol levels dropped 25%.

Though cholestyramine and other resins have been prepared and have been orally administered, their use has not been widely accepted. Specifically, the resins possess an unpleasant sandy texture and must be ingested in large amounts. Additionally, the administration of these resins has been observed to cause nausea and constipation, and the resins have been found to lack the chemical specificity that is necessary to interact exclusively with bile acids; thus, frequently drugs, food materials and other anionic materials in the body will interact with the resin and will reduce the efficiency of its bile acid removal.

SUMMARY OF THE INVENTION

An agent for reducing the cholesterol level in the blood of a warm blooded animal is disclosed which comprises a plurality of vesicles prepared from a non-toxic, non-biodegradable, semi-permeable material, and a quantity of a bile acid sequestrant provided in liquid form. The sequestrant may be present in an amount of up to 90% by volume of the volume capacity of each vesicle. The vesicles are porous to permit the ingress of bile acids, and preferably selectively permit the passage of bile acids having molecular weights no greater than about 1,000 daltons.

The vesicles are non-toxic and indigestible and are therefore passed directly through the system and excreted in the feces. The bile acids pass into the vesicles where they are precipitated by the sequestrant and retained therein.

The sequestrant is selected from polyamines and iron complexes, as these materials are unlikely to diffuse out of the vesicle. Further, due to the ability of the bile acids to exist in an uncharged state, it is preferable to provide a surface charge on the outer surface of the vesicle, as it would prevent the ingress of undesired agents, while permitting the bile acids that are in part uncharged at neutral pH, to pass through.

The method of the present invention comprises administering the cholesterol reducing agent in amounts sufficient to effect the reduction in cholesterol level in the blood. In particular, the method comprises ingesting a plurality of the vesicles filled with the bile acid sequestrant, and preferably by oral administration. The vesicles may be prepared for convenience in capsules or the like, which may then be periodically ingested and thereafter release the vesicles.

The agent and method of the present invention overcome the difficulties of interference with other bodily functions and medications, and discomfort, as the sequestrants are unable to leave the vesicles, and are selected for their specificity of reaction with the bile acids.

The vesicles may be prepared from a variety of non-toxic polymeric materials adapted to form flexible, semi-permeable hollow structures. The filled vesicles may be prepared by a variety of methods known in the art.

Accordingly, it is a principal object of the present invention to provide an agent for reducing the cholesterol level in the blood of a warm blooded animal, which specifically acts to remove bile acids from the body of the animal.

It is a further object of the present invention to provide an agent as aforesaid which does ot unfavorably interact with the system and organs of the animal.

It is a yet further object of the present invention to provide an agent as aforesaid which does not cause adverse side effects in the body.

Other objects and advantages will become apparent to those skilled in the art from a consideration of the ensuing description.

DETAILED DESCRIPTION

The present invention relates to an agent for reducing the level of cholesterol in the blood of a warm blooded animal, and is particularly intended for administration to humans to counteract the incidence of atherosclerosis. As discussed earlier, research has determined that a relationship exists between the level of cholesterol in the blood, and the frequency and severity of cardio-vascular ailments and related death.

The present reducing agents comprise a plurality of vesicles or hollow spherical structures, prepared from flexible polymeric materials that are non-toxic and cannot be digested or otherwise degraded by exposure to body fluids, and which provide a selective permeability to permit the ingress of bile acids. Suitable polymeric materials are well known and may optionally possess a surface electrical charge as discussed in detail, infra. Thus, the vesicles may be prepared from materials selected from the group consisting of polystyrene, polyvinyl chloride, polyoxyethylene, polyoxypropylene, polyacrylamide, cellulose acetate, a copolymer of polystyrene sulfonate-vinyl benzyl trimethylammonium chloride, polyvinyl pyridine, polyacrylic acid and polyethylene terephthalate. These materials are presented as illustrative of suitable polymeric materials and the invention is not limited thereto.

The vesicles may be prepared in a variety of ways to a variety of sizes. Naturally, the smaller size vesicles provide a greater surface area for the absorption of bile acids, and preferably, the vesicle size may range from about 1 to about 1000 μm. In a preferred embodiment, the vesicles of the present invention may be 60 μm.

The vesicles are filled with a bile acid sequestrant which is specifically selected on several grounds. Firstly, it must be capable of precipitating bile acids without causing any unfavorable side effects in the body. Secondly, the sequestrant must be incapable of escaping from the vesicles into the surrounding fluid environment of the body. This further insures against any unfavorable interactions with body fluids and body functions, including medication prescribed for other purposes.

The bile acid sequestrants are generally selected from iron complexes and polyamines which are non-toxic, and incapable of diffusing out of the vesicle once placed therein. Both groups of materials are additionally noted as they are particularly effective in selectively precipitating bile acids. The bile acid sequestrants may be selected from the group consisting of poly N,N dimethyl-3,5-dimethylene piperidinium chloride, 1,5 dimethyl-1,5-diazoundecamethylene polymethylbromide, polydiallyl dimethylammonium chloride, polyethyleneimine, hydroxylethylated polyethyleneimine, polyvinylimine hydrochloride, polyvinylbenzyl trimethylammonium chloride, iron dextran complexes, and saccharated iron oxide. Of the foregoing sequestrants, 1,5, dimethyl-1,5-diazoundecamethylene polymethylbromide is preferred. Naturally, however, the foregoing materials are illustrative of bile acid sequestrants possessing the specificity in other qualities outlined earlier, however, the invention is not to be limited thereto and includes other bile acid sequestrants possessing comparable qualifications.

The sequestrants of the present invention are preferably placed in liquid form within the vesicles, and are generally disposed in aqueous solutions. For example, poly N,N dimethyl 3,5 dimethylene piperidinium chloride may be utilized as a 20% aqueous solution, polydiallyl dimethyl ammonium chloride may be utilized as a 15% aqueous solution, polyethyleneimine is available as a 33% aqueous solution, and hydroxethylated polyethyleneimine may be utilized in water in a 30% solids concentration.

The bile acid sequestrants are disposed in the vesicles in an amount of up to 90% by volume of the total volume of the vesicle. Thus, the vesicle is provided with an interior space which permits it to accept the bile acids which diffuse therein. In particular, the vesicles operate by permitting the selective passage of the bile acids into the bile acid sequestrant, whereupon a precipitation reaction occurs. The precipitate is thereafter retained in the complexed form within the vesicle. Moreover, the precipitation reaction results in the separation of certain chemically unrelated liquid components of the bile acids, whereby the precipitated bile acid occupies a reduced volume. Thus, each of the vesicles may precipitate and retain a fairly large percentage of bile acid, and the vesicles will not be caused to expand beyond their initial size. This has the advantage of discouraging impaction or constipation of the gut, which can occur in the instance where the vesicles, like the prior art resin materials, expand in size.

As noted earlier, vesicle size may vary depending upon the amount of bile acids that it is desired to remove from the body. In particular, individual vesicle size may range, for example, from 1 to 1000 μm, and may preferably be about 60 μm.

As noted earlier, the vesicles must be permeable to the bile acids, and are preferably capable of selectively excluding those materials that are either disruptive to the bile acid precipitation process, or should be retained in the body fluid. Thus, the vesicles are provided with a plurality of pores, which are preferably of a size to permit the passage of bile acids having molecular weights up to 1,000 daltons. As most bile acids have molecular weights of approximately 800 daltons, those materials having molecular weights exceeding 1,000 daltons are likely to be undesirable and would therefore be excluded. In a particular embodiment of the present invention, the pore sizes of the vesicles may be about 20 Å. Naturally, this particular pore size is illustrative of one embodiment of the present invention and the invention is not contemplated as limited thereto.

As noted earlier, the vesicles may be adapted to further selectively exclude extraneous materials, by the provision of an electrical charge on their outer surface. Specifically, the charges may be disposed in the pores to selectively repel undesirable ionic materials. The utility of the electrical charge in the present invention is due to the observation that at neutral pH, bile acids exist in part as an uncharged species, and would therefore pass through the pores unaffected by the electrical charge. Once inside the vesicles, the bile acids would become ionized again, and would thereafter precipitate with the sequestrants. As many of the materials which it is desired to exclude exist in the body fluids as ions, the electrical charge disposed on the vesicles and in the pores may be negative, positive or a combination of the two.

As discussed earlier, the polymeric materials from which the vesicles are prepared may be selected so as to possess the desired surface charge after the vesicle is formed, or the vesicles may be subsequently treated to provide such charge. Thus, the polymeric material may possess a particular charge, and suitable polymeric materials may be selected from neutrally charged materials, positively charged materials, negatively charged materials, and materials possessing both a positive and negative charge. For example, neutral polymeric materials may be selected from polystyrene, polyvinyl chloride, polyoxyethylene, polyoxypropylene, polyacrylamide and cellulose acetate; a positively charged material may comprise polyvinyl pyridine; negatively charged materials may be selected from polyacrylic acid and polyethylene terephthalate; and a material possessing a combined positive and negative charge may be polystyrene sulfonate-vinylbenzyl trimethyl ammonium chloride copolymer. As stated earlier, the foregoing materials are illustrative and not limitative of the invention.

The present invention also concerns a method for reducing the cholesterol level in the blood, which comprises administering the sequestrant-filled vesicles described above. The method of administration may vary in accordance with well known techniques, and may preferably be by oral ingestion. Particularly, oral ingestion may be accomplished by dispersing the vesicles in an inner liquid such as water which may then be swallowed by the patient, or by placing a quantity of the vesicles in a capsule made from a fluid soluble material such as gelatin, which could be orally ingested and, upon the break down of the capsule, would release the vesicles into the digestive tract i.e. the stomach and the intestines.

The quantity and frequency of administration may naturally vary and would be based primarily upon the level of cholesterol in the patients system. For example, the present cholesterol reducing agent may be administered to humans on a daily basis, in an amount sufficient to precipitate from about 1 to about 3 grams of bile acid per day. The present method is naturally not limited to this illustrative scheme.

The reducing agent of the present invention may be prepared by a variety of well known methods for spherulization of resins and liquid encapsulation. For example, the technique of coacervation, wherein a contained liquid is surrounded and thereafter capsulated by the film former in liquid form, was developed and first commercialized in connection with carbon transfer sheets having ink retained in the transfer layer, and may be employed herein.

The vesicles may also be prepared, for example, by a further method wherein the vesicle membrane and the sequestering agent may be coextruded, with a needle located in the center of the extrusion die. The membrane material would flow along the outer surface of the needle and the sequestrant would flow from the open end of the needle. The vesicles would be formed by pulsing the flow of the vesicle-forming plastic material to form bubbles with the liquid sequestrant entrained therein.

The foregoing methods are merely representative of a variety of techniques that may be useful, and the invention is accordingly not to be limited thereto.

The present invention will be better understood from a consideration of the following illustrative example.

EXAMPLE

Vesicles were prepared from a copolymer of polystyrene sulfonate and vinylbenzyl trimethyl ammonium chloride, and were filled with a quantity of 1,5-dimethyl-1,5-diazoundecamethylene polymethylbromide, in aqueous solution. The film-forming material was injected around a needle-like structure having a central orifice from which the sequestrant issues. The resin flow was provided in a pulsating manner and the spherical vesicles were thereby formed. The vesicles were found to be approximately 60 μm in size with pores averaging 20 Å in size. The vesicles possessed both positive and negative surface charges at the pores, and the sequestrant occupied approximately 90% of their volume.

I claim:

1. An agent for reducing the cholesterol level in the blood of a warm blooded animal comprising a plurality of vesicles prepared from a non-toxic, non-biodegradable, semi-permeable material and a quantity of a bile acid sequestrant provided in liquid form,
   wherein said sequestrant is selected from the group consisting of tetra heptylammonium chloride, poly N,N dimethyl-3,5-dimethylene piperidinium chloride, 1,5 dimethyl-1,5-diazoundecamethylene polymethylbromide, polyvinylamine HCl, polyvinylbenzyl trimethylammonium chloride, iron dextran complex and saccharated iron oxide.

2. The agent of claim 1 wherein said sequestrant is present in said vesicles in an amount by volume of up to about 90% of the volume of said vesicle.

3. The agent of claim 1 wherein said vesicles are prepared from a material selected from the group consisting of polystyrene, polyvinyl chloride, polyoxyethylene, polyoxypropylene, polyacrylamide, cellulose acetate, a copolymer of polystyrene sulfonate-vinyl benzyl trimethylammonium chloride, polyvinyl pyridine, polyacrylic acid and polyethylene terephthalate.

4. The agent of claim 1 wherein said vesicles selectively permit the passage therein of bile acids having a molecular weight no greater than about 1,000 daltons.

5. The agent of claim 1 wherein said vesicles are disposed within a digestible capsule, and said capsule is administered orally.

6. The agent of claim 1 wherein said vesicles range in size from about 1 to about 1000 μm.

7. The agent of claim 1 wherein said vesicles define a plurality of pores having a size of about 20 Å.

8. An agent for reducing the cholesterol level in the blood of a warm blooded animal comprising a plurality of vesicles prepared from a non-toxic, non-biodegradable, semi-permeable material and a quantity of a bile acid sequestrant provided in liquid form,
   wherein said vesicles are prepared from a non-toxic, semi-permeable material which possesses a net electrical charge along the surface thereof, and said electrical charge comprises a combination of a positive charge and a negative charge.

9. A method for lowering the level of cholesterol in the blood of a warm blooded animal which comprises:
   A. administering to the digestive tract of the animal an effective amount of non-toxic bile acid sequestrant, said bile acid sequestrant provided in liquid form within a plurality of selectively permeable, non-biodegradable vesicles; and
   B. lowering the concentration of bile acids present in said digestive tract, by sequestering and removing from said digestive tract at least a portion of said bile acids;
   wherein the lowering of said bile acid concentration will effect a reduction in the amount of cholesterol in said blood by promoting an increase in the hepatic conversion of cholesterol to bile acid.

10. The method of claim 9 wherein said sequestrant is selected from the group consisting of tetra heptylammonium chloride, poly N,N dimethyl-3,5-dimethylene piperidinium chloride, 1,5 dimethyl-1,5-diazoundecamethylene polymethylbromide, polyethyleneimine, hydroxyethylated polyethyleneimine, polyvinylamine HCl, polyvinylbenzyl trimethylammonium chloride, iron dextran complex and saccharated iron oxide.

11. The method of claim 9 wherein said vesicles are prepared from a material selected from the group consisting of polystyrene, polyvinyl chloride, polyoxyethylene, polyoxypropylene, polyacrylamide, cellulose acetate, a copolymer of polystyrene sulfonate-vinyl benzyl trimethylammonium chloride, polyvinyl pyridine, polyacrylic acid and polyethylene terephthalate.

12. The method of claim 9 wherein said vesicles define a plurality of pores having size of about 20 Å.

13. The method of claim 9 wherein said vesicles range in size from about 1 to about 1000 μm.

14. The method of claim 9 wherein said vesicles selectively permit the passage therein of bile acids having a molecular weight no greater than about 1,000 daltons.

15. The method of claim 9 wherein said sequestrant occupies no more than about 90% of the volume of said vesicles.

16. The method of claim 9 wherein said vesicles are disposed within a digestible capsule, and said capsule is administered orally.

17. The method of claim 9 wherein said vesicles is prepared from a non-toxic, semi-permeable material which possesses at least one electrical charge along the surface thereof.

18. The method of claim 17 wherein said electrical charge is a combination of positive and negative charges.

* * * * *